United States Patent
Calverley et al.

(10) Patent No.: US 6,310,226 B1
(45) Date of Patent: Oct. 30, 2001

(54) VITAMIN D ANALOGUES

(75) Inventors: Martin John Calverley, Herlev; Henrik Pedersen, Roskilde, both of (DK)

(73) Assignee: Leo Pharmaceutical Products Ltd., Ballerup (DK)

( * ) Notice: Subject to any disclaimer, the term of this patent is extended or adjusted under 35 U.S.C. 154(b) by 0 days.

(21) Appl. No.: 09/297,387

(22) PCT Filed: Oct. 27, 1997

(86) PCT No.: PCT/DK97/00472

§ 371 Date: Apr. 30, 1999

§ 102(e) Date: Apr. 30, 1999

(87) PCT Pub. No.: WO98/18759

PCT Pub. Date: May 7, 1998

(30) Foreign Application Priority Data

Oct. 30, 1996 (GB) .................................................. 9622590

(51) Int. Cl.$^7$ .................. A61K 31/593; C07C 401/00
(52) U.S. Cl. .................. 552/653; 552/653; 514/167
(58) Field of Search .................. 552/653; 514/167

(56) References Cited

U.S. PATENT DOCUMENTS

| | | | |
|---|---|---|---|
| 5,532,391 | * 7/1996 | DeLuca et al. | 552/653 |
| 5,552,392 | 9/1996 | DeLuca et al. | . |
| 5,710,142 | * 1/1998 | Calverly et al. | 514/167 |
| 5,750,746 | * 5/1998 | DeLuca et al. | 552/653 |
| 5,817,648 | * 10/1998 | Kutner et al. | 514/167 |

FOREIGN PATENT DOCUMENTS

| | | |
|---|---|---|
| 633245 | 1/1995 | (EP) . |
| 7-188281 | 7/1995 | (JP) . |
| 91/00271 | 1/1991 | (WO) . |
| 92/03414 | 3/1992 | (WO) . |
| 93/19044 | 9/1993 | (WO) . |

OTHER PUBLICATIONS

Carter et al., Chemotherapy of cancer, Second edition, A Wiley Medical Punlication, John Wiley & sons, 1981, N.Y.*

* cited by examiner

*Primary Examiner*—Sabiha Qazi
(74) *Attorney, Agent, or Firm*—Pillsbury Winthrop LLP

(57) ABSTRACT

The present invention relates to compounds of formula (I) in which formula X is hydrogen or hydroxy; $R^1$ and $R^2$ which may be the same or different, stand for hydrogen or $C_1$–$C_5$ hydrocarbyl; or $R^1$ and $R^2$, taken together with the carbon atom bearing the group X, can form a $C_3C_8$ carbocyclic ring; Q is methylene, ethylene, tri- or tetra-methylene and may optionally be substituted with an oxy group, —$OR^3$, in which $R^3$ is hydrogen, methyl or ethyl; Y is either a single bond or $C_1$–$C_2$ hydrocarbylene; and one or more carbons with in $R^1$, $R^2$, and/or Y may optionally be substituted with one or more fluorine atoms, or with a hydroxyl group. The compounds show anti-inflammatory and immunomodulating effects as well as strong activity in inducing differentiation and inhibiting undesirable proliferation of certain cells.

9 Claims, No Drawings

VITAMIN D ANALOGUES

This invention relates to a hitherto unknown class of compounds which shows strong activity in inducing differentiation and inhibiting undesirable proliferation of certain cells, including skin cells and cancer cells, as well as immunomodulating and anti-inflammatory effects, to pharmaceutical preparations containing these compounds, to dosage units of such preparations, and to their use in the treatment and/or prophylaxis of diseases characterized by abnormal cell differentiation and/or cell proliferation such as e.g. psoriasis and other disturbances of keratinization, HIV-associated dermatoses, wound healing, cancer, including skin cancer, and of diseases of, or imbalance in, the immune system, such as host versus graft and graft versus host reaction and transplant rejection, and autoimmune diseases, such as discoid and systemic lupus erythematosus, diabetes mellitus and chronic dermatoses of autoimmune type, e.g. scleroderma and pemphigus vulgaris, and inflammatory diseases, such as rheumatoid arthritis and asthma, as well as a number of other disease states including hyperparathyroidism, particularly secondary hyperparathyroidism associated with renal failure, cognitive impairment or senile dementia (Alzheimer's disease) and other neurodegenerative diseases, hypertension, acne, alopecia, skin atrophy, e.g. steroid induced skin atrophy, skin ageing, including photo-ageing, and to their use for promoting osteogenesis and treating/preventing osteoporosis and osteomalacia.

The compounds of the invention constitute a novel class of vitamin D analogues represented by the general formula I:

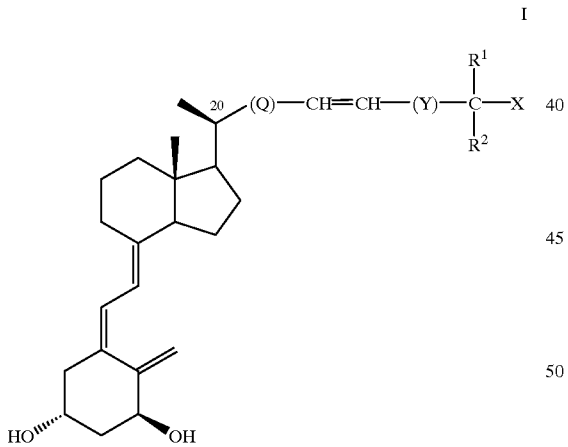

in which formula X is hydrogen or hydroxy; $R^1$ and $R^2$ which may be the same or different, stand for hydrogen or $C_1$–$C_5$ hydrocarbyl; or $R^1$ and $R^2$, taken together with the carbon atom bearing the group X, can form a $C_3$–$C_8$ carbocyclic ring, Q is methylene, ethylene, tri- or tetramethylene and may optionally be substituted with an oxy group, —$OR^3$, in which $R^3$ is hydrogen, methyl or ethyl; Y is either a single bond or $C_1$–$C_2$ hydrocarbylene; and one or more carbons within $R^1$, $R^2$, and/or Y may optionally be substituted with one or more fluorine atoms, or with a hydroxyl group.

In the context of this invention, the expression hydrocarbyl (/hydrocarbylene) indicates the radical (/diradical) obtained after removal of 1 (/2) hydrogen atom(/s) from a straight, branched or cyclic, saturated or unsaturated hydrocarbon.

Examples of $R^1$ and $R^2$ when taken separately include, but are not limited to, hydrogen, methyl, trifluoromethyl, hydroxymethyl, ethyl, (1- or 2-)hydroxyethyl, vinyl, ethynyl, normal-, iso- and cyclopropyl, propen-2-yl, and 3-pentyl. Examples of $R^1$ and $R^2$ when taken together include ethylene, tri-, tetra- and pentamethylene.

Examples of Q with an oxy substituent include but are not limited to, hydroxymethylene, (1- or 2-)hydroxyethylene, (1-, 2- or 3-)hydroxytrimethylene, and corresponding diradicals in which the hydroxy is etherified with methyl or ethyl.

Examples of Y (when not a single bond), include but are not limited to, methylene, hydroxymethylene, difluoromethylene, ethylene, ethylidene (:CH—$CH_3$), CH=CH, C—C, (1- or 2-)hydroxyethylene.

The compounds of the formula I comprise more than one diastereo-isomeric form (E and Z configurations of the side chain double bond, and additionally for example R and S configurations at the carbon bearing the group X when $R^1$ and $R^2$ are different from each other and from X, and E or Z configurations when a double bond is present in the groups Y or R(1 or 2)). The invention covers all these diastereoisomers in pure form and also mixtures thereof. In addition, prodrugs of I in which one or more of the hydroxy groups are masked as groups that can be reconverted to hydroxy groups in vivo are also envisaged.

The compounds I in which X is hydroxy are the preferred ones, but the compounds I in which X is hydrogen are actually another type of prodrug. These compounds are relatively inactive in vitro, but are converted to active compounds of formula I by enzymatic side chain hydroxylation at one or more sites in the —(Y)$CHR^1R^2$ portion of the molecule after administration to the patient.

The compounds I may be obtained in crystalline form either directly by concentration from an organic solvent or by crystallisation or recrystallisation from an organic solvent or mixture of said solvent and a co-solvent that may be organic or inorganic, such as water. The crystals may be isolated in essentially solvent-free form or as a solvate, such as a hydrate. The invention covers all crystalline modifications and forms and also mixtures thereof.

A number of vitamin D analogues have recently been described that show some degree of selectivity in favour of the cell differentiation inducing/cell proliferation inhibiting activity in vitro as compared with the effects on calcium metabolism in vivo (as measured in increased serum calcium concentration and/or increased urinary calcium excretion), which adversely limit the dosage that can safely be administered. One of the first of these to appear, calcipotriol (INN) or calcipotriene (USAN), has been developed on the basis of this selectivity and is now recognized world-wide as an effective and safe drug for the topical treatment of psoriasis.

A study with another analogue (EB 1089) selected on this basis supports the concept that systemically administered vitamin D analogues may inhibit breast cancer cell proliferation in vivo at sub-toxic doses (Colston, K. W. et al., Biochem. Pharmacol. 44, 2273–2280 (1992)).

Promising immunosuppressive activities of vitamin D analogues have been reviewed (Binderup, L., Biochem.

Pharmacol. 43, 1885–1892 (1992)). Thus, a series of 20-epi-vitamin D analogues has been identified as potent inhibitors of T-lymphocyte activation in vitro (Binderup, L. et al., Biochem. Pharmacol. 42, 1569–1575 (1991)). Two of these analogues, MC 1288 and KH 1060, systemically administered, have shown immunosuppressive activities in vivo in experimental animal models. Additive or synergistic effects were observed in combination with low-dose cyclosporin A. KH 1060, alone or in combination with cyclosporin A, has also been shown to prevent autoimmune destruction of transplanted islets in diabetic NOD mice (Bouillon, R. et al. In: Vitamin D, Proceedings of the Ninth Workshop on Vitamin D, Orlando, Fla., Walter de Gruyter, Berlin, 1994, pp 551–552). MC 1288 was able to prolong survival of cardiac and small bowel grafts in rats (Johnsson, C. et al. In: Vitamin D, Proceedings of the Ninth Workshop on Vitamin D, Orlando, Fla., Walter de Gruyter, Berlin, 1994, pp 549–550). However, in all these studies, the dosages of the analogues that produced significant immunosuppression also induced increases in serum calcium levels. There is therefore a continuing need for new analogues with an acceptable combination of prolonged therapeutic activity and minimum toxic effects.

The compounds of the present invention provide a hitherto undisclosed series of 1α-hydroxy-20-epi-vitamin D analogues characterised by the presence of a distal carbon-carbon double bond in the side chain, i.e. positioned in such a way that no double-bonded atom is directly connected to C-20. [A series of 20-epi-vitamin D analogues that contain no side chain double bond or a 22,23-double bond (C-22 is bonded directly to C-20) is disclosed in International Patent Application with Publication number WO91/00271. Reports of compounds having the natural configuration at C-20 and containing a 23,24- or a 24,24a-double bond have appeared (Uskokovic, M. R. et al. In: Vitamin D: Gene Regulation, Structure-Function Analysis and Clinical Application, edited by Norman, A. W., Bouillon, R. and Thomasset, M. Berlin: Walter de Gruyter, 1991, pp. 139–145, Baggiolini E. G.; et al. U.S. Pat. No. 5,087,619-A (1992), Chodynski M. et al., Steroids 56, 311–315 (1991)).] Since the filing of the present application, an application has been published (Kutner, A.; et al. EP 742,203 (1996)) disclosing a series that appears formally to overlap with the compounds 1. However, inspection of the said application once again reveals that exclusively compounds having the natural configuration at C-20 are envisaged, since despite the ambiguity of the general formula no mention of the configuration is made and only intermediates having the natural configuration are invoked. It may be mentioned that the single exemplified compound is in fact the 20-epimer of compound 0106. The exemplified compound is noted to be no more potent ("equally active" p. 13, line 27) than the natural vitamin D hormone (calcitriol) in its effect on cancer cell differentiation. In contrast, our tests with compound 0106 show it to be at least 10-times more potent. Similarly, three other compounds of the present invention (0101, 0103, 0105) were consistently found to be more potent in their effects on cancer cells than their 20-epimers synthesised for comparison purposes. Indeed, the series of compounds now disclosed have been discovered to possess exceptionally high cancer cell proliferation inhibiting activities, combined with high immunosuppressive activities.

A compound of formula I may be prepared by the general method of Scheme 1. In this Scheme, the vitamin D nucleus building block aldehyde II, in which the aldehyde carbon is positioned appropriately to generate the side chain double bond indicated in formula 1, is the starting material. In the following, the symbol $Q_a$ indicates that this linking group may either be identical to Q in the compound I, or alternatively may be a group that can be converted to Q at any subsequent stage in the synthesis. Furthermore, the identity of $Q_a$ may change from intermediate to intermediate along the reaction sequence. However the actual identity will be apparent from the particular context.

Following the synthetic scheme as depicted:

1. II is reacted with a reagent to introduce the side chain double bond and extend the chain. Typically this would be a Wittig (or Wittig-type) reaction or a Julia-type reaction). These methods are well known in the field of vitamin D chemistry. Intermediates having the E or the Z configuration of the double bond formed under non-stereospecific reaction conditions may be conveniently separated at this stage.

The symbol $Y_a$ is used to indicate optional identity with or convertibility to Y (see above for analogous use of $Q_a$), and the symbol W bears an analogous relationship to the group $C(R^1)(R^2)(X)$ in I.

The remaining steps in the synthesis involve:

2. Optional conversion of the group $Q_a$ to Q;
3. Optional conversion of the group $Y_a$ to Y;
4. Optional conversion of the group W to $C(R^1)(R^2)(X)$;
5. Triplet-sensitized photoisomerisation of the vitamin D triene (5E to 5Z); and
6. Removal of the vitamin D nucleus silyl protecting groups;

The sequence of steps 1 through 6 may be altered (e.g. the photoisomerisation step (5) may precede the reaction (step 1) introducing the double bond), and several steps may be combined (e.g. the conditions of the desilylation step (6) may also effect a deprotection of the alcohol group X (step 4). Examples of conditions and reagents for the specified reactions (i.e. for steps 5 and 6) are well known in the prior art of vitamin D analogue synthesis. Alternative routes than those illustrated to any one of the intermediates II, III or IV or the compound I are available and will be obvious to the man skilled in the art.

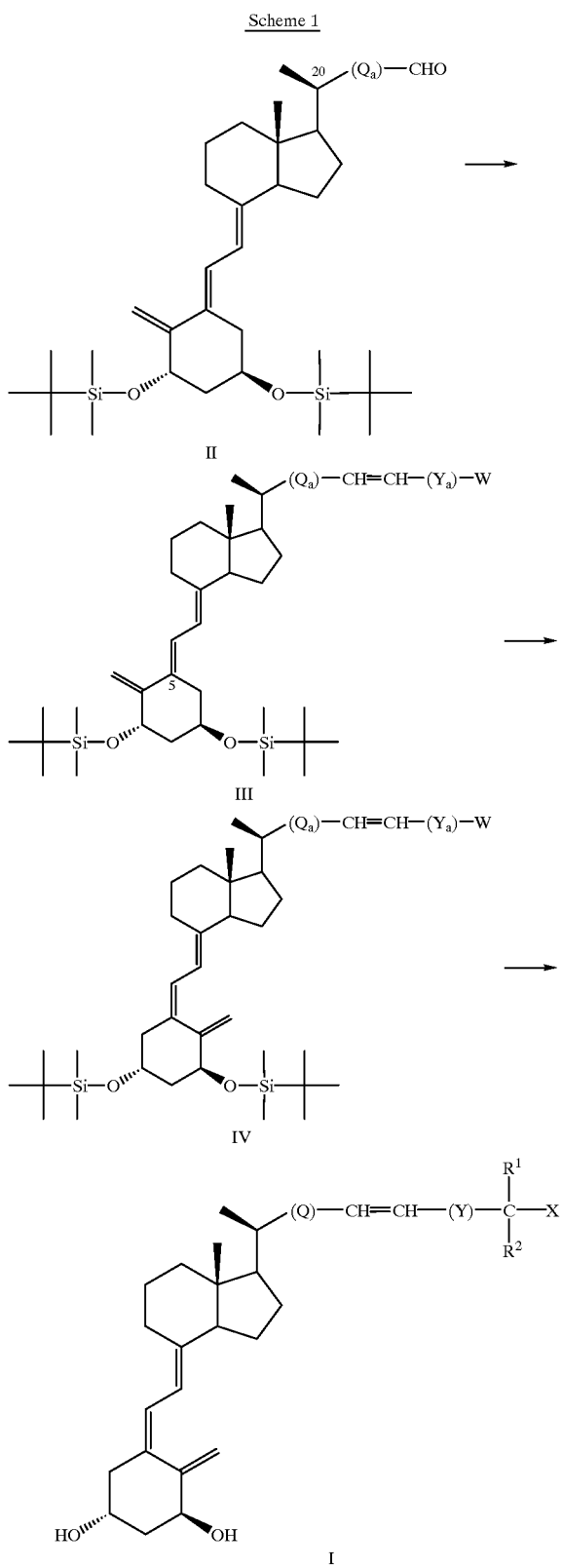

Scheme 1

The present compounds are intended for use in pharmaceutical compositions that are useful in the local or systemic treatment of human and veterinary disorders as described above.

The present compounds may be used in combination with other pharmaceuticals or treatment modalities. In the treatment of psoriasis the present compounds may be used in combination with e.g. steroids or with other treatments e.g. light- or UV-light-treatment or the combined PUVA-treatment. In the treatment of cancer the present compounds may be used in combination with other anti-cancer drugs or anti-cancer treatments, such as radiation treatment. In the prevention of graft rejection and graft versus host reaction, or in the treatment of auto-immune diseases, the present compounds may advantageously be used in combination with other immunosuppressive/immunoregulating drugs or treatments, e.g. with cyclosporin A.

The amount required of a compound of formula I (hereinafter referred to as the active ingredient) for therapeutic effect will, of course, vary both with the particular compound, the route of administration and the mammal under treatment. The compounds of the invention can be administered by the parenteral, intra-articular, enteral or topical routes. They are well absorbed when given enterally and this is the preferred route of administration in the treatment of systemic disorders. In the treatment of dermatological disorders like psoriasis or eye diseases topical or enteral forms are preferred.

While it is possible for an active ingredient to be administered alone as the raw chemical, it is preferable to present it as a pharmaceutical formulation. Conveniently, the active ingredient comprises from 0.1 ppm to 0.1% by weight of the formulation.

The formulations, both for veterinary and for human medical use, of the present invention thus comprise an active ingredient in association with a pharmaceutically acceptable carrier therefore and optionally other therapeutic ingredient(s). The carrier(s) must be "acceptable" in the sense of being compatible with the other ingredients of the formulations and not deleterious to the recipient thereof.

The formulations include e.g. those in a form suitable for oral, ophthalmic, rectal, parenteral (including subcutaneous, intramuscular and intravenous), transdermal, intra-articular and topical, nasal or buccal administration.

By the term "dosage unit" is meant a unitary, i.e. a single dose that is capable of being administered to a patient, and which may be readily handled and packed, remaining as a physically and chemically stable unit dose comprising either the active material as such or in admixture with solid or liquid pharmaceutical diluents or carriers.

The formulations may conveniently be presented in dosage unit form and may be prepared by any of the methods well known in the art of pharmacy. All methods include the step of bringing the active ingredient into association with the carrier that constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

Formulations for rectal administration may be in the form of a suppository incorporating the active ingredient and a carrier, or in the form of an enema.

Formulations suitable for parenteral administration conveniently comprise a sterile oily or aqueous preparation of the active ingredient that is preferably isotonic with the blood of the recipient. Transdermal formulations may be in the form of a plaster.

Formulations suitable for intra-articular or ophthalmic administration may be in the form of a sterile aqueous preparation of the active ingredient that may be in microcrystalline form, for example, in the form of an aqueous microcrystalline suspension. Liposomal formulations or biodegradable polymer systems may also be used to present the active ingredient for both intra-articular and ophthalmic administration.

Formulations suitable for topical or ophthalmic administration include liquid or semi-liquid preparations such as liniments, lotions, gels, applicants, oil-in-water or water-in-oil emulsions such as creams, ointments or pastes; or solutions or suspensions such as drops.

Formulations suitable for administration to the nose or buccal cavity include powder, self-propelling and spray formulations, such as aerosols and atomizers.

In addition to the aforementioned ingredients, the formulations of this invention may include one or more additional ingredients, such as diluents, binders, preservatives, etc.

The compositions may further contain other therapeutically active compounds usually applied in the treatment of the above mentioned pathological conditions, such as other immunosuppressants in the treatment of immunological diseases, or steroids in the treatment of dermatological diseases.

The present invention further concerns a method for treating patients suffering from one of the above pathological conditions, said method consisting of administering to a patient in need of treatment an effective amount of one or more compounds of formula I, alone or in combination with one or more other therapeutically active compounds usually applied in the treatment of said pathological conditions. The treatment with the present compounds and/or with further therapeutically active compounds may be simultaneous or with intervals.

In the systemic treatment daily doses of from 0.001–2 $\mu$g per kilogram bodyweight, preferably from 0.002–0.3 $\mu$g/kg of mammal bodyweight, for example 0.003–0.3 $\mu$g/kg of a compound of formula I are administered, typically corresponding to a daily dose for an adult human of from 0.2 to 25 $\mu$g. In the topical treatment of dermatological disorders, ointments, creams or lotions containing from 0.1–500 $\mu$g/g, and preferably from 0.1–100 $\mu$g/g, of a compound of formula I are administered. For topical use in ophthalmology ointments, drops or gels containing from 0.1–500 $\mu$g/g, and preferably from 0.1–100 $\mu$g/g, of a compound of formula I are administered. The oral compositions are formulated, preferably as tablets, capsules, or drops, containing from 0.05–50 $\mu$g, preferably from 0.1–25 $\mu$g, of a compound of formula I, per dosage unit.

The invention is further illustrated by the following non-limiting Preparations and Examples:

Preparations and Examples

The exemplified compounds I are listed in Table 1, whereas the starting materials and intermediates of general formulae II, III, and IV are listed in Table 2. Table 3 lists compounds that are intermediates in the illustrated interconversion of Compounds II. The structures of these intermediates are represented in Scheme 2, and the reactions involved are well known in the field of vitamin D chemistry.

The following standard abbreviations are used throughout this disclosure: Me=methyl; Et=ethyl; TBS=t-butyldimethylsilyl.

TABLE 1

Exemplified Compounds I (Details are provided for compounds where an Example Number is given; the other compounds may be prepared using analogous reaction sequences from the appropriate Compound of Table 2)

| Compound Number | Example Number | Q | Configuration of double bond | Y | X | $R^1$ | $R^2$ |
|---|---|---|---|---|---|---|---|
| 0101 | 01 | $CH_2$ | E | single bond | OH | Me | Me |
| 0102 | 02 | $CH_2$ | Z | single bond | OH | Me | Me |
| 0103 | 03 | $CH_2$ | E | single bond | OH | Et | Et |
| 0104 | 04 | $CH_2$ | Z | single bond | OH | Et | Et |
| 0105 | 05 | $(CH_2)_2$ | E | single bond | OH | Et | Et |
| 0106 | 06 | $(CH_2)_3$ | E | single bond | OH | Me | Me |
| 0107 | 07 | $(CH_2)_3$ | Z | single bond | OH | Me | Me |
| 0108 | 08 | CH(OH) # | E | single bond | OH | Me | Me |
| 0109 | 09 | CH(OH) ## | E | single bond | OH | Me | Me |
| 0110 | 10 | CH(OEt) # | E | single bond | OH | Me | Me |
| 0111 | 11 | CH(OH)—$CH_2$ ## | E | single bond | OH | Et | Et |
| 0112 | 12 | CH(OMe)—$CH_2$ ## | E | single bond | OH | Et | Et |
| 0113 | 13 | $(CH_2)_4$ | E | single bond | OH | Me | Me |
|  |  | $CH_2$ | E | single bond | OH |  | —$(CH_2)_4$— |
|  |  | $CH_2$ | E | single bond | OH | ethynyl | ethynyl |
| 0114 | 14 | $CH_2$ | E | single bond | OH | H ### | cyclopropyl |
|  | (14) | $CH_2$ | E | single bond | OH | H #### | cyclopropyl |
|  | (14) | $CH_2$ | E | single bond | OH | H ##### | cyclopropyl |
|  |  | $CH_2$ | E | single bond | OH | H ### | 3-pentyl |
|  |  | $CH_2$ | E | single bond | H | Me | Me |
| 0115 | 15 | $CH_2$ | E | $CH_2$ | OH | Et | Et |

TABLE 1-continued

Exemplified Compounds I (Details are provided for compounds where an Example Number is given; the other compounds may be prepared using analogous reaction sequences from the appropriate Compound of Table 2)

| Compound Number | Example Number | Q | Configuration of double bond | Y | X | R¹ | R² |
|---|---|---|---|---|---|---|---|
| 0116 | 16 | $CH_2$ | E | CH=CH (E) | OH | Et | Et |
|  |  | $CH_2$ | E | $CF_2$ | OH | Et | Et |
|  |  | $CH_2$ | E | CH(OH) | OH | Et | Et |
|  |  | $CH_2$ | E | single bond | OH | H #### | 1-fluorocyclopropyl |

Footnotes to Table 1
\# 22-configuration: S;
\#\# 22-configuration: R;
\#\#\# Mixture of epimers;
\#\#\#\# R-configuration;
\#\#\#\#\# S-configuration

TABLE 2

Starting materials and intermediates of general formulae II, III and IV (Details are provided for compounds where a Preparation Number is given; the other compounds may be prepared using analogous reaction sequences from the appropriate Compound II)

| Prep. No. | Compound Number | Type | Q(a) | Configuration of double bond | Y(a) | W |
|---|---|---|---|---|---|---|
| * | 0201 | II | single bond |  |  |  |
| ** | 0202 | II | $CH_2$ |  |  |  |
| ** | 0203 | II | $(CH_2)_2$ |  |  |  |
| ** | 0204 | II | $(CH_2)_3$ |  |  |  |
| 05 | 0205 | II | CH(OEt) # |  |  |  |
| 06 | 0206 | II | CH(O-TBS) # |  |  |  |
| 07 | 0207 | II | CH(O-TBS)—$CH_2$ ## |  |  |  |
| 08 | 0208 | II | CH(O-TBS) ## |  |  |  |
| 09 | 0301a | III | $CH_2$ | E | single bond | $CO_2Me$ |
| 09 | 0302a | III | $CH_2$ | Z | single bond | $CO_2Me$ |
| 10 | 0303a | III | $(CH_2)_2$ | E | single bond | $CO_2Me$ |
| 11 | 0304a | III | $(CH_2)_3$ | E | single bond | $CO_2Me$ |
| 11 | 0305a | III | $(CH_2)_3$ | Z | single bond | $CO_2Me$ |
| 12 | 0306a | III | CH(O-TBS) # | E | single bond | $CO_2Me$ |
| 13 | 0307a | III | CH(O-TBS) ## | E | single bond | $CO_2Me$ |
| 14 | 0308a | III | CH(OEt) # | E | single bond | $CO_2Me$ |
| 15 | 0309a | III | CH(O-TBS)—$CH_2$ ## | E | single bond | $CO_2Me$ |
| 16 | 0301b | III | $CH_2$ | E | single bond | $C(OH)(Me)_2$ |
| 17 | 0302b | III | $CH_2$ | Z | single bond | $C(OH)(Me)_2$ |
| 18 | 0303b | III | $(CH_2)_2$ | E | single bond | $C(OH)(Et)_2$ |
| 19 | 0304b | III | $(CH_2)_3$ | E | single bond | $C(OH)(Me)_2$ |
| 20 | 0305b | III | $(CH_2)_3$ | Z | single bond | $C(OH)(Me)_2$ |
| 21 | 0306b | III | CH(O-TBS) # | E | single bond | $C(OH)(Me)_2$ |
| 22 | 0307b | III | CH(O-TBS) ## | E | single bond | $C(OH)(Me)_2$ |
| 23 | 0308b | III | CH(OEt) # | E | single bond | $C(OH)(Me)_2$ |
| 24 | 0309b | III | CH(O-TBS)—$CH_2$ ## | E | single bond | $C(OH)(Et)_2$ |
| 25 | 0401b | IV | $CH_2$ | E | single bond | $C(OH)(Me)_2$ |
| 26 | 0405b | IV | $(CH_2)_2$ | E | single bond | $C(OH)(Et)_2$ |
| 27 | 0406b | IV | $(CH_2)_3$ | E | single bond | $C(OH)(Me)_2$ |
| 28 | 0407b | IV | $(CH_2)_3$ | Z | single bond | $C(OH)(Me)_2$ |
| 29 | 0408b | IV | CH(O-TBS) # | E | single bond | $C(OH)(Me)_2$ |
| 30 | 0409b | IV | CH(O-TBS) ## | E | single bond | $C(OH)(Me)_2$ |
| 31 | 0410b | IV | CH(OEt) # | E | single bond | $C(OH)(Me)_2$ |
| 32 | 0411b | IV | CH(O-TBS)—$CH_2$ ## | E | single bond | $C(OH)(Et)_2$ |
| 33 | 0402b | IV | $CH_2$ | Z | single bond | $C(OH)(Me)_2$ |
| 34 | 0401a | IV | $CH_2$ | E | single bond | $CO_2Me$ |
| 35 | 0402a | IV | $CH_2$ | Z | single bond | $CO_2Me$ |
| 36 | 0403b | IV | $CH_2$ | E | single bond | $C(OH)(Et)_2$ |
| 37 | 0404b | IV | $CH_2$ | Z | single bond | $C(OH)(Et)_2$ |
| 38 | 0207a | II | CH(OMe)—$CH_2$ ## |  |  |  |
| 39 | 0310a | III | CH(OMe)—$CH_2$ ## | E | single bond | $CO_2Me$ |
| 40 | 0310b | III | CH(OMe)—$CH_2$ ## | E | single bond | $C(OH)(Et)_2$ |
| 41 | 0412b | IV | CH(OMe)—$CH_2$ ## | E | single bond | $C(OH)(Et)_2$ |
| 42 | 0204a | II | $(CH_2)_4$ |  |  |  |
| 43 | 0311a | III | $(CH_2)_4$ | E | single bond | $CO_2Me$ |
| 44 | 0311b | III | $(CH_2)_4$ | E | single bond | $C(OH)(Me)_2$ |
| 45 | 0413b | IV | $(CH_2)_4$ | E | single bond | $C(OH)(Me)_2$ |
| 46 | 0312a | III | $CH_2$ | E | single bond | $C(O)C_3H_5$ |
| 47 | 0312b | III | $CH_2$ | E | single bond | $CH(OH)C_3H_5$ |
| 48 | 0414b | IV | $CH_2$ | E | single bond | $CH(OH)C_3H_5$ |

TABLE 2-continued

Starting materials and intermediates of general formulae II, III and IV (Details are provided for compounds where a Preparation Number is given; the other compounds may be prepared using analogous reaction sequences from the appropriate Compound II)

| Prep. No. | Compound Number | Type | Q(a) | Configuration of double bond | Y(a) | W |
|---|---|---|---|---|---|---|
| 49 | 0313b | III | $CH_2$ | E | $CH_2$ | $C(OH)(Et)_2$ |
| 50 | 0415b | IV | $CH_2$ | E | $CH_2$ | $C(OH)(Et)_2$ |
| 51 | 0314a | III | $CH_2$ | E | CH=CH (E) | $CO_2Me$ |
| 52 | 0314b | III | $CH_2$ | E | CH=CH (E) | $C(OH)(Et)_2$ |
| 53 | 0416b | IV | $CH_2$ | E | CH=CH (E) | $C(OH)(Et)_2$ |

Footnotes to Table 2
Descriptions refer to Scheme 1, where applicable.
* Starting material, described in: Calverley, M. J., Tetrahedron, Vol 43, pp 4609–4619 (1987).
** Starting materials, described in: Calverley, M. J. and Pedersen, H. Novel vitamin D analogues, WO 9,410,139-A1 (1994), Preparations 1, 2 and 3, respectively.
\# 22-configuration: S
\#\# 22-configuration: R Scheme 2

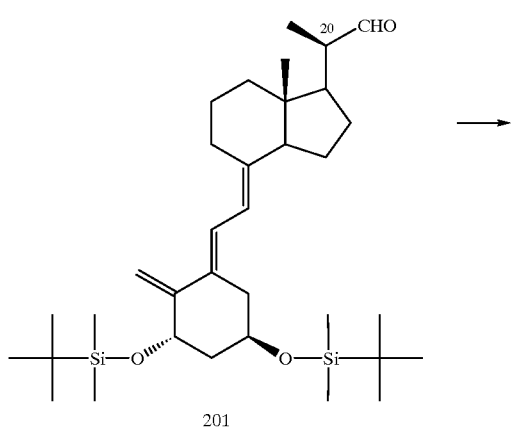

201

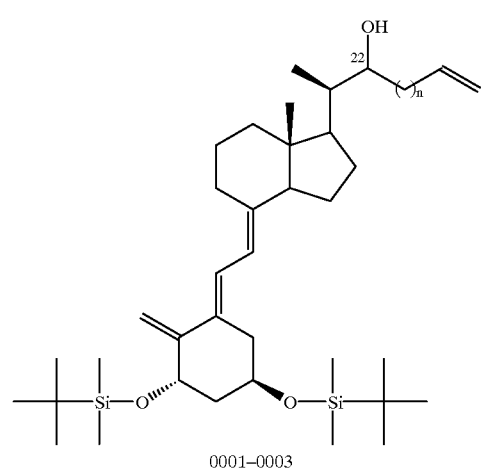

0001–0003

-continued

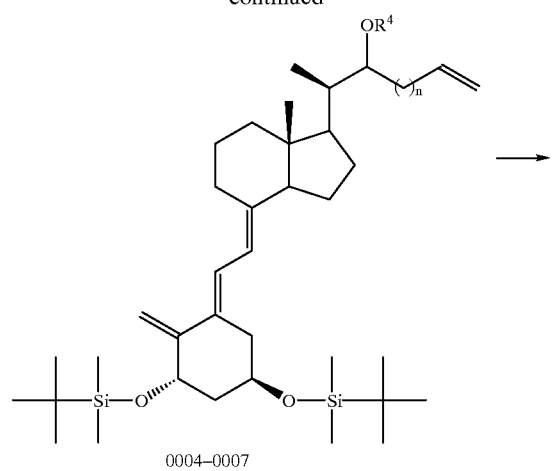

0004–0007

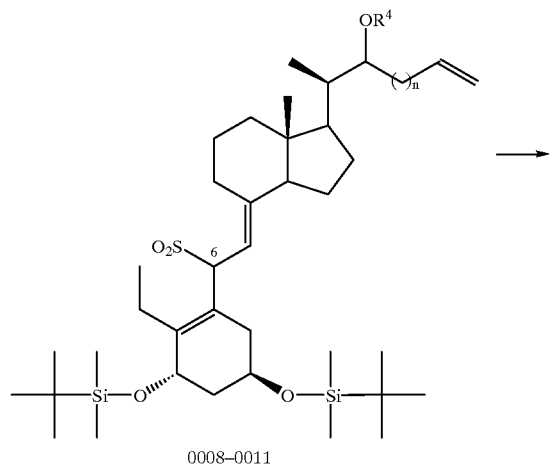

0008–0011

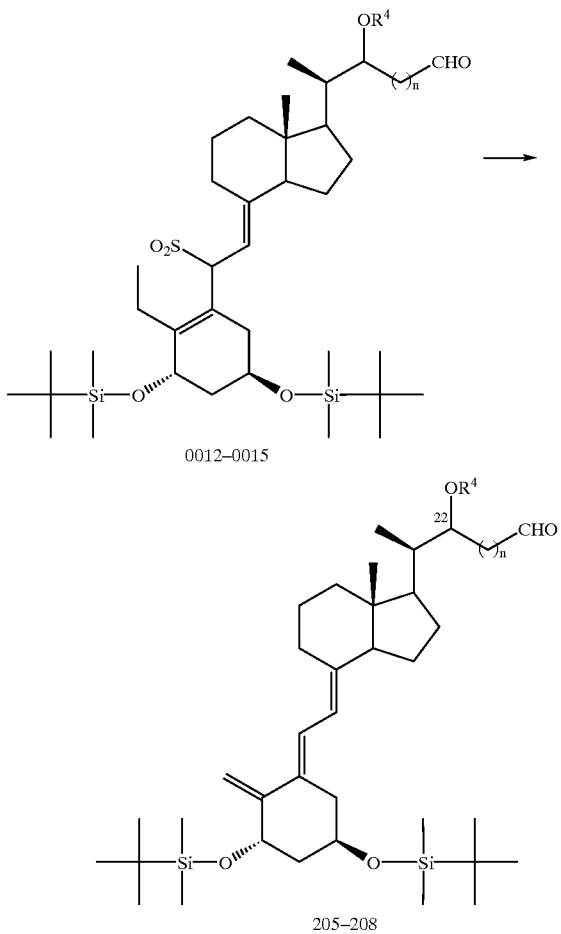

0012–0015

205–208

TABLE 3

Intermediates illustrated for interconversion of Compounds II
(Scheme 2)

| Prep Number | Compound Number | 22-Configuration | n | $R^4$ |
|---|---|---|---|---|
| 1 | 0001 | R | 0 | — |
| 1 | 0002 | S | 0 | — |
| * | 0003 | R | 1 | — |
| 2a | 0004 | R | 0 | Et |
| 2b | 0005 | R | 0 | TBS |
| * | 0006 | R | 1 | TBS |
| 2c | 0006a | R | 1 | Me |
| * | 0007 | S | 0 | TBS |
| 3a | 0008 | R | 0 | Et |
| 3b | 0009 | R | 0 | TBS |
| * | 0010 | R | 1 | TBS |
| 3c | 0010a | R | 1 | Me |
| * | 0011 | S | 0 | TBS |
| 4a | 0012 | S | 0 | Et |
| 4b | 0013 | S | 0 | TBS |
| * | 0014 | R | 1 | TBS |
| 4c | 0014a | R | 1 | Me |
| * | 0015 | R | 0 | TBS |

Footnotes to Table 3
Descriptions refer to Scheme 2, where applicable. The sulphur dioxide adducts (compounds 0008 to 0015) were formed and used as epimeric mixtures at C-6. The first step in each sequence is reaction with the Grignard reagent $CH_2=CH-(CH_2)_n-MgBr$ followed by separation of the intermediate (0001 to 0003) having the required 22-configuration, and the remaining sequences are:

TABLE 3-continued

Intermediates illustrated for interconversion of Compounds II
(Scheme 2)

| Prep Number | Compound Number | 22-Configuration | n | $R^4$ |
|---|---|---|---|---|

0001 -> 0004 -> 0008 -> 0012 -> 0205;
0001 -> 0005 -> 0009 -> 0013 > 0206;
0003 -> 0006 -> 0010 -> 0014 -> 0207;
0003 -> 0006a -> 0010a -> 0014a -> 0207a;
0002 -> 0007 -> 0011 -> 0015 -> 0208.
*Prepared by analogous reactions to the illustrated preparation.

General

Ether refers to diethyl ether. Petroleum ether refers to the pentane fraction. Tetrahydrofuran (THF) was dried over sodium/benzophenone. Reactions were routinely run under an argon atmosphere unless otherwise noted. For the column chromatographic purification of products only the final eluent composition is specified: typically the elution was begun with a mixture containing more petroleum ether.

For $^1H$ nuclear magnetic resonance spectra (300 MHz) chemical shift values (δ) (in ppm) are quoted, unless otherwise specified, for deuteriochloroform solutions relative to internal tetramethylsilane (δ=0.00) or chloroform (δ=7.25). The value for a multiplet, either defined (doublet (d), triplet (t), quartet (q)) or not (m) at the approximate mid-point is given unless a range is quoted (s=singlet, b=broad). Apparent coupling constants (J) are estimated as absolute values (often to the nearest unit) in Hertz for selected defined multiplets. The following partial spectra were common to the particular types of compound described and are therefore not reported individually: For compounds of types II (including the intermediates 0001 to 0007 in Scheme 2) and III: δ0.05 (12H, bs), 0.86 (9H, s), 0.89 (9H, s), 2.30 (1H, bd, J 14), 2.55 (1H, dd, J 5 14), 2.86 (1H, bd), 4.21 (1H, m), 4.52 (1H, m), 4.93 (1H, m), 4.98 (1H, m), 5.81 (1H, d, J 11), 6.45 (1H, d, J 11); compounds of type IV: 0.05 (12H, m), 0.87 (18H, s), 2.20 (1H, dd), 2.44 (1H, dd), 2.81 (H, bd, J 11), 4.18 (H, m), 4.36 (H, m), 4.85 (1H, m), 5.17 (1H, m), 6.00 (H, d, J 11), 6.22 (H, d, J 11); compounds of type I: 2.31 (1H, dd, J 6.5 13), 2.59 (1H, dd, J 3 13), 2.83 (1H, dd, J 4 11), 4.22 (1H, m), 4.42 (1H, m), 5.00 (1H, bs), 5.33 (1H, bs), 6.02 (1H, d, J 11), 6.37 (1H, d, J 11). Some or all of the characteristic signals not included in these common spectra are reported for the individual compounds.

Preparation 01: Compounds 0001 and 0002

To a solution, maintained at about 25° C., of Compound 0201 (2.013 g, 3.5 mmol) in dry THF (6 ml) was added via a syringe vinyl magnesium bromide (1M in THF) (9 mmol). After stirring at the same temperature for 30 min, the reaction mixture was partitioned between ether and saturated ammonium chloride solution. The organic layer was separated, washed with saturated sodium chloride solution, dried over anhydrous magnesium sulphate, and filtered and concentrated in vacuo to give an oil. Purification by chromatography on silica gel (100 g) (eluant: 20% ether in petroleum ether) gave the Title Compounds. 0001 (first eluted): δ0.57 (3 H, s), 0.83 (3 H, d, J 6.6), 1.25 to 2 (14 H, m), 2.07 (1 H, t, J 9), 4.41 (1 H, bs), 5.13 (1 H, dt, J 2 11), 5.22 (1 H, dt, J 2 17), 5.86 (1 H, ddd, J 5 11 17); 0002: d 0.58 (3 H, s), 0.85 (3 H, d, J 7), 1.2 to 2.1 (15 H, m), 4.36 (1 H, m), 5.2 (1 H, bd, J 11), 5.28 (1 H, bd, J 17), 5.92 (1 H, ddd, J 5 11 17).

Preparation 02a: Compound 0004

To a solution, maintained at about −40° C., of 18-crown-6 (0.35 g, 1.33 mmol) and Compound 0001 (0.637 g, 1.06 mmol) in dry THF (20 ml) was added portionwise potassium hydride (20% dispersion in oil) (3 mmol) followed by bromoethane (1 ml, 14 mmol). After stirring at the same temperature for 10 min and thereafter at 25° C. for 90 min, the reaction mixture was partitioned between ether and water. The organic layer was separated, washed with saturated sodium chloride solution, dried over anhydrous magnesium sulphate, and filtered and concentrated in vacuo to give an oil. Purification by chromatography on silica gel (150 g) (eluant: 02% ether in petroleum ether) gave the Title Compound. $\delta$0.54 (3 H, s), 0.8 to 0.97 (3 H, d), 1.05 to 1.97 (13 H, m), 1.16 (3 H, t, J 7), 2.04 (1 H, t, J 9), 3.25 (1 H, m), 3.51 (1 H, m), 3.75 (1 H, dd, J 3.4 7) 5.13 (1 H, m), 5.15 (1 H, m), 5.76 (1 H, m).

Preparation 02b: Compound 0005

To a solution, maintained at about 5° C., of 2,6-lutidine (0.75 ml, 6.5 mmol) and Compound 0001 (0.955 g, 1.67 mmol) in dry dichloromethane (5 ml) was added via a syringe t-butyldimethylsilyl trifluoromethanesulphonate (0.860 g, 3.3 mmol). After stirring at the same temperature for 1 h, the reaction mixture was partitioned between ether and water. The organic layer was separated, washed with saturated sodium chloride solution, dried over anhydrous magnesium sulphate, and filtered and concentrated in vacuo to give an oil. Purification by chromatography on silica gel (100 g) (eluant: 02% ether in petroleum ether) gave the Title Compound.

Preparation 2c: Compound 0006a

To a solution, maintained at about −40° C., of 18-crown-6 (0.35 g, 1.33 mmol) and Compound 0003 (0.617 g, 1.0 mmol) in dry THF (20 ml) was added portionwise potassium hydride (20% dispersion in oil) (3 mmol) followed by iodomethane (0.9 ml, 14 mmol). After stirring at the same temperature for 10 min and thereafter at 25° C. for 90 min, the reaction mixture was partitioned between ether and water. The organic layer was separated, washed with saturated sodium chloride solution, dried over anhydrous magnesium sulphate, and filtered and concentrated in vacuo to give an oil. Purification by chromatography on silica gel (150 g) (eluant: 02% ether in petroleum ether) gave the Title Compound.

Preparation 03a: Compound 0008

To a solution, maintained at about −40° C., of Compound 0004 (0.630 g, 1 mmol) in ether (6 ml) was added rapidly liquid sulphur dioxide (100 mmol). After stirring at the same temperature for 10 min and thereafter at −10° C. for 40 min, the reaction mixture was concentrated in vacuo. The residue was dried in high vacuum to give a solid. Without further purification, this product containing the Title Compound was used in the next step.

Preparation 03b: Compound 0009

The title compound was prepared analogously to the procedure of Preparation 03a but using Compound 0005 (1.060 g, 1.48 mmol) in ether (3 ml) as starting material.

Preparation 03c: Compound 0010a

The title compound was prepared analogously to the procedure of Preparation 03a but using Compound 0006a (0.820 g, 1.3 mmol) in ether (3 ml) as starting material.

Preparation 04a: Compound 0012

A solution, maintained at about −70° C., of Compound 0008 obtained as the crude product from Compound 0004 (0.630 g, 1 mmol) in dichloromethane (8 ml) and methanol (3 ml) was treated with ozonised oxygen until starting material could no longer be detected by thin layer chromatography. The solution was then purged with nitrogen and triphenylphosphine (0.4 g) was added. After stirring at the same temperature for 10 min and thereafter at 0° C. for 30 min, the reaction mixture was concentrated in vacuo. The residue was dried in high vacuum to give a solid. Purification by chromatography on silica gel (100 g) (eluant: 30% ether in petroleum ether) gave the Title Compound.

Preparation 04b: Compound 0013

The title compound was prepared analogously to the procedure of Preparation 03a but using as starting material Compound 0009 obtained as the crude product from Compound 0005 (1.48 mmol) in dichloromethane (12 ml) and methanol (4 ml). Triphenylphosphine (0.650 g) was employed.

Preparation 04c: Compound 0014a

The title compound was prepared analogously to the procedure of Preparation 03a but using as starting material Compound 0010a obtained as the crude product from Compound 0006a (1.3 mmol) in dichloromethane (12 ml) and methanol (4 ml). Triphenylphosphine (0.650 g) was employed.

Preparation 05: Compound 0205

To a vigorously stirred mixture, maintained at about 25° C., of Compound 0012 (0.300 g, 0.43 mmol) in toluene (5 ml) was added 5% aqueous sodium bicarbonate solution (5 ml) and the mixture was degassed. After stirring at the same temperature for 5 min and thereafter at 85° C. for 90 min, the reaction mixture was partitioned between ether and water. The organic layer was separated, washed with saturated sodium chloride solution, dried over anhydrous magnesium sulphate, and concentrated in vacuo to give an oil. Purification by chromatography on silica gel (30 g) (eluant: 20% ether in petroleum ether) gave the Title Compound. $\delta$0.59 (3 H, s), 0.75 to 0.95 (3 H, d), 1.15 to 2.15 (14 H, m), 1.26 (3 H, t, J 7), 3.42 (1 H, m), 3.71 (1 H, m), 3.82 (1 H, m), 9.72 (1 H, d, J 1).

Preparation 06: Compound 0206

The title compound was prepared analogously to the procedure of Preparation 05 but using Compound 0013 (0.468 g, 0.59 mmol) as starting material in toluene (7 ml) and 5% aqueous sodium bicarbonate solution (7 ml). Purification by chromatography on silica gel (50 g) (eluant: 02% ether in petroleum ether) gave the Title Compound. $\delta$0.06 (6 H, s), 0.55 (3 H, s), 0.8 to 0.95 (3 H, d), 0.94 (9 H, s), 1.15 to 2.1 (14 H, m), 4.09 (1 H, m), 9.62 (1 H, m).

Preparation 07: Compound 0207

The title compound was prepared analogously to the procedure of Preparation 06 but using Compound 0014 as starting material. $\delta$0.05 (6 H, s), 0.49 (3 H, s), 0.85 (3 H, d), 0.88 (9 H, s), 1.15 to 2.05 (14 H, m), 2.52 (2H, m), 4.24 (1 H, m), 9.77 (1 H, t, J 2).

Preparation 08: Compound 0208

The title compound was prepared analogously to the procedure of Preparation 06 but using Compound 0015 as starting material.

Preparation 09: Compounds 0301a and 0302a

To a mixture, maintained at about −20° C., of benzoic acid (10 mg) and methyl(triphenylphosphoranylidene)acetate (0.646 g, 1.93 mmol) in dry methanol (8 ml) was added dropwise Compound 0202 (0.630 g, 1.07 mmol) in dry THF (2 ml). After stirring at the same temperature for 15 min and thereafter at 22° C. overnight, the reaction mixture was partitioned between ethyl acetate and water. The organic layer was separated, washed with saturated sodium chloride solution, dried over anhydrous magnesium sulphate, and concentrated in vacuo to give an oil. Purification by chromatography on silica gel (100 g) (eluant: 02% ethyl acetate in petroleum ether) gave the Title Compounds. 0301a (first eluted): $\delta$0.56 (3 H, s), 0.84 (3 H, d), 1.1 to 2.15 (15 H, m), 2.49 (1 H, m), 3.71 (3 H, s), 5.8 (1 H, d, J 16), 6.94 (1 H, m); 0302a: $\delta$0.57 (3 H, s), 0.75 to 1 (3 H, d), 1.2 to 2.1 (14 H, m), 2.6 (1 H, m), 2.86 (1 H, m), 3.69 (3 H, s), 5.82 (1 H, m), 6.25 (1 H, d).

Preparation 10: Compound 0303a

To a solution, maintained at about 25° C., of Compound 0203 (0.360 g, 0.6 mmol) in degassed toluene (20 ml) was added in one portion methyl (triphenylphosphoranylidene) acetate (0.400 g, 1.2 mmol). After stirring at the same temperature for 5 min and thereafter at 100° C. for 2 h, the reaction mixture was partially concentrated in vacuo and diluted with ether and methanol. The solution was set aside to crystallise and filtered to give the Title Compound. Needles; m.p. 82–83° C.; $\delta$0.53 (3 H, s), 0.85 (3 H, d), 1.2 to 2.15 (17 H, m), 2.27 (1 H, m), 3.72 (3 H, s), 5.81 (1 H, d, J 16), 6.97 (1 H, dt, J 7 16).

Preparation 11: Compounds 0304a and 0305a

To a solution, maintained at about 25° C., of Compound 0204 (0.110 g, 0.16 mmol) in degassed toluene (6 ml) was added in one portion methyl(triphenylphosphoranylidene) acetate (0.130 g, 0.39 mmol). After stirring at the same temperature for 5 min and thereafter at 100° C. for 3 h, the reaction mixture was partially concentrated in vacuo and diluted with ether. The solution was set aside to crystallise and filtered and concentrated in vacuo to give an oil. Purification by chromatography on silica gel (30 g) (eluant: 05% ether in petroleum ether) gave the Title Compounds. 0304a: $\delta$0.52 (3 H, s), 0.83 (3 H, d, J 6.4), 1.1 to 2.05 (18 H, m), 2.16 (2 H, m), 3.71 (3 H, s), 5.8 (1 H, d, J 16), 6.97 (1 H, dt, J 7 16); 0305a (first eluted): $\delta$0.52 (3 H, s), 0.84 (3 H, d), 1.1 to 2.05 (18 H, m), 2.63 (2 H, m), 3.69 (3 H, s), 5.76 (1 H, dt, J 2 11.5), 6.22 (1 H, dt, J 7.5 11.5).

Preparation 12: Compound 0306a

The title compound was prepared analogously to the procedure of Preparation 11 but using Compound 0206 (0.520 g, 0.72 mmol) as starting material. Methyl (triphenylphosphoranylidene)acetate (0.500 g, 1.5 mmol) was employed. $\delta$0.05 (6 H, s), 0.48 (3 H, s), 0.8 to 0.95 (3 H, d), 0.92 (9 H, s), 1.1 to 2.05 (14 H, m), 3.74 (3 H, s), 4.24 (1 H, m), 5.94 (1 H, dd, J 1.5 16), 6.95 (1 H, dd, J 5 16).

Preparation 13: Compound 0307a

The title compound was prepared analogously to the procedure of Preparation 12 but using Compound 0208 as starting material.

Preparation 14: Compound 0308a

The title compound was prepared analogously to the procedure of Preparation 11 but using Compound 0205 (0.216 g, 0.34 mmol) as starting material. Methyl (triphenylphosphoranylidene)acetate (0.220 g, 0.66 mmol) was employed. Purification by chromatography on silica gel (15 g) (eluant: 05% ether in petroleum ether) gave the Title Compound. $\delta$0.53 (3 H, s), 0.85 (3 H, d), 1.15 to 2 (13 H, m), 1.18 (3 H, t, J 7), 2.05 (1 H, t, J 9), 3.31 (1 H, m), 3.48 (1 H, m), 3.74 (3 H, s), 4.01 (1 H, m), 5.93 (1 H, dd, J 1 16), 6.87 (1 H, dd, J 6 16).

Preparation 15: Compound 0309a

The title compound was prepared analogously to the procedure of Preparation 11 but using Compound 0207 (0.045 g, 0.06 mmol) as starting material in degassed toluene (2 ml). Methyl(triphenylphosphoranylidene)acetate (0.045 g, 0.12 mmol) was employed. Purification by chromatography on silica gel (30 g) (eluant: 10% ether in petroleum ether) gave the Title Compound. $\delta$0.05 (6 H, s), 0.46 (3 H, s), 0.83 (3 H, d, J 7), 0.88 (9 H, s), 1.2 to 2.1 (14 H, m), 2.32 (2 H, m), 3.72 (3 H, s), 3.81 (1 H, m), 5.83 (1 H, d, J 16), 6.9 (1 H, dt, J 8 16).

Preparation 16: Compound 0301b

To a solution, maintained at about −20° C., of Compound 0301a (0.091 g, 0.14 mmol) in dry ether (5 ml) was added via a syringe methyl-lithium (1.6 M in ether) (1.6 mmol). After stirring at the same temperature for 1 h, the reaction mixture was quenched with water and partitioned between ether and water. The organic layer was separated, washed with saturated sodium chloride solution, dried over anhydrous magnesium sulphate, and concentrated in vacuo to give an oil. Purification by chromatography on silica gel (50 g) (eluant: 05% ethyl acetate in petroleum ether) gave the Title Compound. $\delta$0.55 (3 H, s), 0.81 (3 H, d), 1 to 2.06 (16 H, m), 1.29 (6 H, s), 2.3 (1 H, m), 5.57 (2 H, m).

Preparation 17: Compound 0302b

The title compound was prepared analogously to the procedure of Preparation 16 but using Compound 0302a (0.184 g, 0.286 mmol) as starting material in dry THF (3 ml). 10% ethyl acetate in petroleum ether was employed as eluant. $\delta$0.55 (3 H, s), 0.85 (3 H, d), 1 to 2.08 (15 H, m), 1.35 (6 H, s), 2.18 (1 H, m), 5.28 (1 H, m), 5.5 (1 H, d, J 12).

Preparation 18: Compound 0303b

The title compound was prepared analogously to the procedure of Preparation 16 but using Compound 0303a (0.237 g, 0.36 mmol) in dry THF (3 ml) as starting material in dry THF (3 ml) and ethyl-lithium (1.4 M in ether) (0.9 mmol) as reagent. 20% ether in petroleum ether was employed as eluant. $\delta$0.52 (3 H, s), 0.85 (6 H, t, J 7.5), 0.85 (3 H, d), 1.1 to 2.25 (19 H, m), 1.51 (2 H, q, J 7.5), 1.52 (2 H, q, J 7.5), 5.38 (1 H, d, J 16), 5.57 (1 H, dt, J 7 16).

Preparation 19: Compound 0304b

The title compound was prepared analogously to the procedure of Preparation 16 but using Compound 0304a (0.067 g, 0.1 mmol) as starting material in dry THF (3 ml) and methyl-lithium (1.6 M in ether) (0.5 mmol). Purification by chromatography on silica gel (15 g) (eluant: 20% ether in petroleum ether) gave the Title Compound. $\delta$0.52 (3 H, s), 0.83 (3 H, d, J 6.5), 1.1 to 2.1 (21 H, m), 1.29 (6 H, s), 5.59 (2 H, m).

Preparation 20: Compound 0305b

The title compound was prepared analogously to the procedure of Preparation 16 but using Compound 0305a (0.055 g, 0.082 mmol) as starting material in dry THF (3 ml)

and methyl-lithium (1.6 M in ether) (0.4 mmol). Purification by chromatography on silica gel (15 g) (eluant: 20% ether in petroleum ether) gave the Title Compound. δ0.53 (3 H, s), 0.83 (3 H, d, J 6.4), 1.1 to 2.1 (19 H, m), 1.36 (6 H, s), 2.15 to 2.37 (2 H, m), 5.3 (1 H, dt, J 7.4 12), 5.47 (1 H, bd, J 12).

Preparation 21: Compound 0306b

The title compound was prepared analogously to the procedure of Preparation 16 but using Compound 0306a (0.100 g, 0.13 mmol) as starting material in dry THF (3 ml) and methyl-lithium (1.6 M in ether) (0.64 mmol). Purification by chromatography on silica gel (15 g) (eluant: 20% ether in petroleum ether) gave the Title Compound. δ0.00 (3 H, s), 0.03 (3 H, s), 0.49 (3 H, s), 0.82 (3 H, d), 0.9 (9 H, s), 1.15 to 2.05 (15 H, m), 1.31 (6 H, s), 4.08 (1 H, dd, J 3 6), 5.6 (1 H, dd, J 6 16), 5.68 (1 H, d, J 16).

Preparation 22: Compound 0307b

The title compound was prepared analogously to the procedure of Preparation 16 but using Compound 0307a (0.073 g, 0.094 mmol) as starting material in dry THF (3 ml) and methyl-lithium (1.6 M in ether) (0.5 mmol). Purification by chromaography on silica gel (15 g) (eluant: 20% ether in petroleum ether) gave the Title Compound. δ0.00 (3 H, s), 0.03 (3 H, s), 0.54 (3 H, s), 0.8 (3 H, d, J 6.8), 0.89 (9 H, s), 1.15 to 2.05 (15 H, m), 1.32 (6 H, s), 4.3 (1 H, m), 5.64 (1 H, dd, J 5 16), 5.79 (1 H, dd, J 1 16).

Preparation 23: Compound 0308b

The title compound was prepared analogously to the procedure of Preparation 16 but using Compound 0308a (0.133 g, 0.19 mmol) as starting material in dry THF (3 ml) and methyl-lithium (1.6 M in ether) (0.96 mmol). Purification by chromatography on silica gel (15 g) (eluant: 20% ether in petroleum ether) gave the Title Compound. δ0.53 (3 H, s), 0.85 (3 H, d), 1 to 1.97 (14 H, m), 1.16 (3 H, t, J 7), 1.33 (6 H, s), 2.03 (1 H, t, J 9.5), 3.24 (1 H, m), 3.48 (1 H, m), 3.77 (1 H, dd, J 3 7), 5.57 (1 H, dd, J 7 16), 5.73 (1 H, d, J 16).

Preparation 24: Compound 0309b

The title compound was prepared analogously to the procedure of Preparation 16 but using Compound 0309a (0.024 g, 0.03 mmol) in dry THF (2 ml) as starting material in dry THF (3 ml) and ethyl-lithium (1.2 M in ether) (0.1 mmol) as reagent. Purification by chromatography on silica gel (15 g) (eluant: 10% ether in petroleum ether) gave the Title Compound. δ0.05 (6 H, s), 0.46 (3 H, s), 0.83 (3 H, d), 0.85 (6 H, t), 0.89 (9 H, s), 1.15 to 2.05 (15 H, m), 1.51 (4 H, q, J 7.5), 2.2 (2 H, m), 3.82 (1 H, t, J 7), 5.42 (1 H, d, J 16), 5.53 (1 H, dt, J 7 16).

Preparation 25: Compound 0401b

To a solution, maintained at about 10° C., of Compound 0301b (0.091 g, 0.141 mmol) in degassed dichloromethane (10 ml) was added anthracene (0.091 g, 0.512 mmol) and triethylamine (0.1 ml). After being irradiated with a UV lamp (type: Hanau TQ 718Z2) at the same temperature for 22 min, the reaction mixture was partially concentrated in vacuo and diluted with petroleum ether. The solution was filtered and concentrated in vacuo to give an oil. Purification by chromatography on silica gel (50 g) (eluant: 20% ethyl acetate in petroleum ether) gave the Title Compound. δ0.54 (3 H, s), 0.81 (3 H, d), 1.15 to 2.05 (16 H, m), 1.3 (6 H, s), 2.32 (1 H, m), 5.57 (2 H, m).

Preparation 26: Compound 0405b

The title compound was prepared analogously to the procedure of Preparation 25 but using Compound 0303b (0.120 g, 0.17 mmol) as starting material in dichloromethane (7 ml) with anthracene (0.150 g, 0.84 mmol). The irradiation time was 35 min. Purification by chromatography on silica gel (15 g) (eluant: 10% ether in petroleum ether) gave the Title Compound.

Preparation 27: Compound 0406b

The title compound was prepared analogously to the procedure of Preparation 25 but using Compound 0304b (0.063 g, 0.093 mmol) as starting material in degassed toluene (4 ml) with anthracene (0.075 g, 0.42 mmol). The irradiation time was 35 min. Purification by chromatography on silica gel (15 g) (eluant: 20% ether in petroleum ether) gave the Title Compound. δ0.51 (3 H, s), 0.82 (3 H, d, J 6.4), 1.05 to 2.05 (21 H, m), 1.29 (6 H, s), 5.59 (2 H, m).

Preparation 28: Compound 0407b

The title compound was prepared analogously to the procedure of Preparation 27 but using Compound 0305b (0.033 g, 0.049 mmol) as starting material with anthracene (0.036 g, 0.2 mmol). Purification by chromatography on silica gel (15 g) (eluant: 20% ether in petroleum ether) gave the Title Compound.

Preparation 29: Compound 0408b

The title compound was prepared analogously to the procedure of Preparation 27 but using Compound 0306b (0.080 g, 0.103 mmol) as starting material with anthracene (0.030 g, 0.17 mmol). Purification by chromatography on silica gel (15 g) (eluant: 20% ether in petroleum ether) gave the Title Compound. δ−0.01 (3 H, s), 0.02 (3 H, s), 0.48 (3 H, s), 0.82 (3 H, d, J 6.8), 0.88 (9 H, s), 1.15 to 2 (15 H, m), 1.3 (3 H, s), 1.31 (3 H, s), 4.07 (1 H, dd, J 3 6), 5.6 (1 H, dd, J 6 16), 5.67 (1 H, d, J 16).

Preparation 30: Compound 0409b

The title compound was prepared analogously to the procedure of Preparation 27 but using Compound 0307b as starting material.

Preparation 31: Compound 0410b

The title compound was prepared analogously to the procedure of Preparation 27 but using Compound 0308b (0.060 g, 0.087 mmol) as starting material with anthracene (0.020 g, 0.12 mmol). δ0.52 (3 H, s), 0.86 (3 H, d), 1.05 to 1.95 (14 H, m), 1.16 (3 H, t, J 7), 1.32 (3 H, s), 1.33 (3 H, s), 1.98 (1 H, t, J 9), 3.24 (1 H, m), 3.48 (1 H, m), 3.76 (1 H, dd, J 3 7), 5.57 (1 H, dd, J 7 16), (5.73 (1 H, d, J 16).

Preparation 32: Compound 0411b

The title compound was prepared analogously to the procedure of Preparation 27 but using Compound 0309b (0.020 g, 0.025 mmol) as starting material with anthracene (0.010 g, 0.06 mmol). Purification by chromatography on silica gel (15 g) (eluant: 10% ether in petroleum ether) gave the Title Compound.

Preparation 33: Compound 0402b

The title compound was prepared analogously to the procedure of Preparation 25 but using Compound 0302b (0.137 g, 0.213 mmol) as starting material in dichloromethane (6 ml) with anthracene (0.137 g, 0.77 mmol). The irradiation time was 25 min. Purification by chromatography on silica gel (50 g) (eluant: 05% ethyl acetate in petroleum ether) gave the Title Compound. δ0.54 (3 H, s), 0.8 to 1 (3 H, d), 1.15 to 2.08 (15 H, m), 1.36 (6 H, s), 2.18 (1 H, m), 2.59 (1 H, m), 5.28 (1 H, m), 5.5 (1 H, d, J 12).

Preparation 34: Compound 0401a

The title compound was prepared analogously to the procedure of Preparation 25 but using Compound 0302a (0.389 g, 0.6 mmol) as starting material in dichloromethane (6 ml) with anthracene (0.389 g, 2.2 mmol). The irradiation time was 30 min. Purification by chromatography on silica gel (50 g) (eluant: 02% ethyl acetate in petroleum ether) gave the Title Compound. δ0.54 (3 H, s), 0.84 (3 H, d), 1.2 to 2.15 (15 H, m), 2.45 (1 H, m), 3.72 (3 H, s), 5.8 (1 H, d, J 16), 6.94 (1 H, d).

Preparation 35: Compound 0402a

The title compound was prepared analogously to the procedure of Preparation 25 but using Compound 0301a (0.153 g, 0.238 mmol) as starting material in dichloromethane (6 ml) with anthracene (0.153 g, 0.858 mmol). The irradiation time was 25 min. Purification by chromatography on silica gel (50 g) (eluant: 01% ethyl acetate in petroleum ether) gave the Title Compound. δ0.56 (3 H, s), 0.8 to 1 (3 H, d), 1.2 to 2.1 (14 H, m), 2.61 (1 H, m), 2.84 (1 H, m), 3.69 (3 H, s), 5.8 (1 H, d), 6.24 (1 H, m).

Preparation 36: Compound 0403b

The title compound was prepared analogously to the procedure of Preparation 16 but using Compound 0401a (0.252 g, 0.392 mmol) as starting material in dry THF (8 ml) and ethyl-lithium (1.4 M in ether) (2.4 mmol) as reagent. Purification by chromatography on silica gel (50 g) (eluant: 05% ethyl acetate in petroleum ether) gave the Title Compound. δ0.54 (3 H, s), 0.83 (3 H, d), 0.85 (6 H, t), 1.2 to 2.1 (20 H, m), 2.2 (1 H, dd), 2.35 (1 H, m), 5.35 (1 H, d, J 16), 5.54 (1 H, m)

Preparation 37: Compound 0404b

The title compound was prepared analogously to the procedure of Preparation 16 but using Compound 0402a (0.082 g, 0.127 mmol) as starting material in dry THF (3 ml) and ethyl-lithium (1.4 M in ether) (1.2 mmol) as reagent. Purification by chromatography on silica gel (50 g) (eluant: 02% ethyl acetate in petroleum ether) gave the Title Compound. δ0.54 (3 H, s), 0.85 (3 H, d), 0.89 (6 H, t), 1.15 to 2.08 (19 H, m), 2.18 (1 H, m), 2.6 (1 H, m), 5.25 (1 H, d, J 12), 5.39 (1 H, m).

Preparation 38: Compound 0207a

The title compound was prepared analogously to the procedure of Preparation 06 but using Compound 0014a as starting material.

Preparation 39: Compound 0310a

The title compound was prepared analogously to the procedure of Preparation 11 but using Compound 0207a (0.050 g, 0.08 mmol) as starting material in degassed toluene (2 ml). Methyl(triphenylphosphoranylidene)acetate (0.045 g, 0.12 mmol) was employed. Purification by chromatography on silica gel (30 g) (eluant: 10% ether in petroleum ether) gave the Title Compound.

Preparation 40: Compound 0310b

The title compound was prepared analogously to the procedure of Preparation 16 but using Compound 0310a (0.034 g, 0.05 mmol) in dry THF (2 ml) as starting material in dry THF (3 ml) and ethyl-lithium (1.2 M in ether) (0.1 mmol) as reagent. Purification by chromatography on-silica gel (15 g) (eluant: 10% ether in petroleum ether) gave the Title Compound.

Preparation 41: Compound 0412b

The title compound was prepared analogously to the procedure of Preparation 27 but using Compound 0310b (0.018 g, 0.025 mmol) as starting material with anthracene (0.010 g, 0.06 mmol). Purification by chromatography on silica gel (15 g) (eluant: 10% ether in petroleum ether) gave the Title Compound.

Preparation 42: Compound 0204a

The title compound was prepared analogously to the iterative homologation procedure described in: Calverley, M. J. and Pedersen, H. Novel vitamin D analogues, WO 9,410,139-A1 (1994), Preparation 3, but using the tosylate prepared from Compound 10 of that patent. Purification by chromatography on silica gel (100 g) (eluant: 05% ethyl acetate in petroleum ether) gave the Title Compound. δ0.53 (3 H, s), 0.83 (3 H, d), 1.1 to 2.05 (20 H, m), 2.41 (2 H, dt), 9.76 (1 H, t).

Preparation 43: Compound 0311a

The title compound was prepared analogously to the procedure of Preparation 11 but using Compound 0204a (0.380 g, 0.6 mmol) as starting material. Methyl (triphenylphosphoranylidene)acetate (0.500 g, 1.5 mmol) was employed. δ0.52 (3 H, s), 0.83 (3 H, d, J 6.4), 1.1 to 2.05 (20 H, m), 2.16 (2 H, m), 3.71 (3 H, s), 5.8 (1 H, d, J 16), 7.0 (1 H, dt, J 7 16).

Preparation 44: Compound 0311b

The title compound was prepared analogously to the procedure of Preparation 16 but using Compound 0311a (0.069 g, 0.1 mmol) as starting material in dry THF (3 ml) and methyl-lithium (1.6 M in ether) (0.5 mmol). Purification by chromatography on silica gel (15 g) (eluant: 20% ether in petroleum ether) gave the Title Compound. δ0.52 (3 H, s), 0.83 (3 H, d, J 6.5), 1.1 to 2.1 (23H, m), 1.29 (6 H, s), 5.6 (2 H, m).

Preparation 45: Compound 0413b

The title compound was prepared analogously to the procedure of Preparation 25 but using Compound 0311b (0.055 g, 0.08 mmol) as starting material in degassed toluene (4 ml) with anthracene (0.038 g, 0.21 mmol). The irradiation time was 35 min. Purification by chromatography on silica gel (15 g) (eluant: 20% ether in petroleum ether) gave the Title Compound. δ0.51 (3 H, s), 0.82 (3 H, d, J 6.4), 1.05 to 2.05 (23 H, m), 1.29 (6 H, s), 5.6 (2 H, m).

Preparation 46: Compound 0312a

To a solution, maintained at about 25° C., of Compound 0202 (0.120 g, 0.20 mmol) in degassed toluene (6 ml) was added in one portion cyclopropylcarbonylmethylenetriphenylphosphorane (0.138 g, 0.40 mmol). After stirring at the same temperature for 5 min and thereafter at 100° C. for 3 h, the reaction mixture was partially concentrated in vacuo and diluted with ether. The solution was set aside to crystallise and filtered and concentrated in vacuo to give an oil. Purification by chromatography on silica gel (30 g) (eluant: 05% ether in petroleum ether) gave the Title Compound. δ0.57 (3H, s), 0.8 to 0.9 (3H, d), 0.8 to 0.9 (4H, m), 1.07 (1H, m), 2.52 (1H, m), 6.21 (1H, d, J 16), 6.88 (1H, ddd).

Preparation 47: Compound 0312b

To a solution, maintained at about 5° C., of Compound 0312a (0.090 g, 0.14 mmol) in THF (1 ml) and methanol (2 ml) containing cerium chloride hepta-hydrate (0.2 mmol) was added in one portion sodium borohydride (0.02 g, 0.5 mmol). After stirring at the same temperature for 10 min, the reaction mixture was partitioned between ethyl acetate and water. The organic layer was separated, washed with saturated sodium chloride solution, dried over anhydrous magnesium sulphate, and concentrated in vacuo to give an oil. Purification by chromatography on silica gel (30 g) (eluant: 10% ethyl acetate in petroleum ether) gave the Title Compound as a ca. 1:1 mixture of epimers. (The epimers can be separated by chromatography at this stage if required.) δ0.22 (1 H, m), 0.32 (1H, m), 0.5 (2H, m), 0.56 (3H, s), 0.8 to 0.9 (3H, d), 0.98 (1H, m), 2.34 (1 H, m), 3.46 (1H, m), 5.52 (1H, dd, J 6.5 15), 5.62 (1H, dt, J 7 15).

Preparation 48: Compound 0414b

The title compound was prepared analogously to the procedure of Preparation 25 but using Compound 0312b (0.078 g, 0.12 mmol) as starting material in dichloromethane (5 ml) with anthracene (0.015 g, 0.084 mmol). The irradiation time was 35 min. Purification by chromatography on silica gel (15 g) (eluant: 10% ethyl acetate in petroleum ether) gave the Title Compound.

Preparation 49: Compound 0313b

To a solution, maintained at about −25° C., of 3-ethyl-3-hydroxypentyl phenyl sulphone (155 mg, 0.60 mmol) in dry THF (4 ml) was added via a syringe lithium di-isopropylamide (3 ml, 1.2 mmol, of a 0.4 M solution in THF-hexanes, 3:1). After stirring at the same temperature for 30 min, the reaction mixture was cooled to −40° C. for the addition of a solution of Compound 0202 (0.293 g, 0.50 mmol) in THF (2 ml). After stirring at the same temperature for 30 min, benzoyl chloride (0.15 ml, 1.3 mmol) was added dropwise, and the mixture was allowed to warm to room temperature during a further 30 min. The reaction mixture was partitioned between ether and water. The organic layer was separated, washed with saturated sodium chloride solution, dried over anhydrous magnesium sulphate, and filtered and concentrated in vacuo to give an oil. This was redissolved in ethyl acetate (2 ml) and diluted with methanol (12 ml, saturated with and containing suspended disodium hydrogen phosphate). To this solution, maintained at about 5° C., was added ca. 5% sodium amalgam (4 g) and stirring continued at the same temperature 15 h. The reaction mixture was partitioned between ethyl acetate and water (decanting from the mercury) and the organic layer was separated, washed with saturated sodium chloride solution, dried over anhydrous magnesium sulphate, and filtered and concentrated in vacuo to give an oil. Purification by chromatography on silica gel (50 g) (eluant: 10% ether in petroleum ether) gave the Title Compound.

Preparation 50: Compound 0415b

The title compound was prepared analogously to the procedure of Preparation 25 but using Compound 0313b (0.120 g, 0.18 mmol) as starting material in dichloromethane (7 ml) with anthracene (0.075 g, 0.42 mmol). The irradiation time was 35 min. Purification by chromatography on silica gel (15 g) (eluant: 10% ether in petroleum ether) gave the Title Compound.

Preparation 51: Compound 0314a

To a solution, maintained at about 25° C., of Compound 0202 (1.00 g, 1.70 mmol) in chloroform (6 ml) was added in one portion methyl 4-(triphenylphosphoranylidene) crotonate (0.645 g, 1.79 mmol). After stirring at the same temperature for 5 min and thereafter at 60° C. for 24 h, the reaction mixture was partially concentrated in vacuo and diluted with ether. The solution was set aside to crystallise and filtered and concentrated in vacuo to give an oil. Purification by chromatography on silica gel (100 g) (eluant: 01% ethyl acetate in petroleum ether) gave the Title Compound.

Preparation 52: Compound 0314b

The title compound was prepared analogously to the procedure of Preparation 16 but using Compound 0314a (0.20 g, 0.3 mmol) in dry THF (3 ml) as starting material in dry THF (3 ml) and ethyl-lithium (1.4 M in ether) (0.9 mmol) as reagent. 20% ether in petroleum ether was employed as eluant.

Preparation 53: Compound 0416b

The title compound was prepared analogously to the procedure of Preparation 25 but using Compound 0314b (0.104 g, 0.15 mmol) as starting material in dichloromethane (7 ml) with anthracene (0.075 g, 0.42 mmol). The irradiation time was 35 min. Purification by chromatography on silica gel (15 g) (eluant: 10% ether in petroleum ether) gave the Title Compound.

Examples 01 to 16

The following general procedure for removing the silyl protective groups and isolation and purification was employed: To a solution, maintained at about 5° C., of the Compound IV starting material (ca. 0.02 to 0.16 mmol) in dry THF (2 to 5 ml; x ml) was added in one portion tetrabutylammonium fluoride trihydrate (ca 0.2 to 1.6 mmol, y g). After stirring at the same temperature for 5 min and thereafter at 60° C. for 1 h, the reaction mixture was partitioned between ethyl acetate and 5% sodium hydrogen carbonate solution. The organic layer was separated, washed with saturated sodium chloride solution, dried over anhydrous magnesium sulphate, and concentrated in vacuo to give an oil. Purification by chromatography on silica gel (15 g) (eluant: ethyl acetate) gave the Title Compound.

EXAMPLE 01

1(S),3(R),25-Trihydroxy-20(S)-9,10-seco-cholesta-5 (Z),7(E),10(19),-23(E)-tetraene (Compound 0101)

Starting material: Compound 0401b (0.063 g, 0.098 mmol); x=5; y=0.308. δ0.56 (3 H, s), 0.82 (3 H, d), 1.2 to 2.1 (18 H, m), 1.31 (6 H, s), 2.31 (1 H, m), 5.57 (2 H, m).

EXAMPLE 02

1(S),3(R),25-Trihydroxy-20(S)-9,10-seco-cholesta-5 (Z),7(E),10(19),23(Z)-tetraene (Compound 0102)

Starting material: Compound 0402b (0.024 g, 0.037 mmol); x=5; y=0.132. δ0.56 (3 H, s), 0.86 (3 H, d), 1.1 to 1.2 (17 H, m), 1.37 (6 H, s), 2.18 (1 H, m), 2.6 (1 H, m), 5.28 (1 H, m), 5.51 (1 H, d, J 12).

EXAMPLE 03

26,27-Dimethyl-1(S),3(R),25-Tri-hydroxy-20(S)-9, 10-seco-cholesta-5(Z),7(E), 10(19),23(E)-tetraene (Compound 0103)

Starting material: Compound 0403b (0.108 g, 0.16 mmol); x=5; y=0.51. δ0.57 (3 H, s), 0.83 (3 H, d), 0.86 (6 H, t), 1.15 to 2.1 (22 H, m), 2.34 (1 H, m), 5.36 (1 H, d), 5.55 (1 H, m).

EXAMPLE 04

26,27-Dimethyl-1(S),3(R),25-Tri-hydroxy-20(S)-9,
10-seco-cholesta-5(Z),7(E), 10(19),23(Z)-tetraene
(Compound 0104)

Starting material: Compound 0404b (0.036 g, 0.054 mmol); x=5; y=0.17. δ0.56 (3 H, s), 0.86 (3 H, d), 0.9 (6 H, t), 1.2 to 2.1 (21 H, m), 2.18 (1 H, m), 2.6 (1 H, m), 5.26 (1 H, d, J 12), 5.4 (1 H, m).

EXAMPLE 05

1(S),3(R)-Dihydroxy-20(S)-(5'-hydroxy-5'-ethyl-3'(E)-hepten-1'-yl)-9,10-seco-pregna-5(Z),7(E), 10(19)-triene (Compound 0105)

Starting material: Compound 0405b (0.048 g, 0.07 mmol); x=4; y=0.10. δ0.54 (3 H, s), 0.85 (6 H, t, J 7.5), 0.85 (3 H, d, J 6), 1.15 to 2.25 (21 H, m), 1.51 (2 H, q, J 7.5), 1.52 (2 H, q, J 7.5), 5.38 (1 H, d, J 16), 5.57 (1 H, dt, J 7 16).

EXAMPLE 06

1(S),3(R)-Dihydroxy-20(S)-(6'-hydroxy-6'-methyl-4'(E)-hepten-1'-yl)-9,10-seco-pregna-5(Z),7(E), 10(19)-triene (Compound 0106)

Starting material: Compound 0406b (0.043 g, 0.06 mmol); x=3; y=0.21. δ0.54 (3 H, s), 0.83 (3 H, d), 1.05 to 2.1 (23 H, m), 1.3 (6 H, s), 5.6 (2 H, m).

EXAMPLE 07

1(S),3(R)-Dihydroxy-20(S)-(6'-hydroxy-6'-methyl-4'(Z)-hepten-1'-yl)-9,10-seco-pregna-5(Z),7(E),10(19)-triene (Compound 0107)

Starting material: Compound 0407b (0.026 g, 0.04 mmol); x=3; y=0.13. δ0.54 (3 H, s), 0.83 (3 H, d), 1.05 to 2.1 (21 H, m), 1.36 (6 H, s), 2.3 (2 H, m), 5.3 (1 H, dt, J 7 12), 5.47 (1 H, bd, J 12).

EXAMPLE 08

1(S),3(R),22(S),25-Tetrahydroxy-20(R)-9,10-seco-cholesta-5(Z),7(E),-10(19)-,23(E)-tetraene
(Compound 0108)

Starting material: Compound 0408b (0.069 g, 0.09 mmol); x=3; y=0.25. δ0.57 (3 H, s), 0.82 (3 H, d, J 6.5), 1.2 to 2.1 (18 H, m), 1.33 (6 H, s), 4.42 (1 H, m), 5.67 (1 H, dd, J 5 16), 5.81 (1 H, dd, J 1 16).

EXAMPLE 09

1(S),3(R),22(R),25-Tetrahydroxy-20(R)-9,10-seco-cholesta-5(Z),7(E),10(19)-,23(E)-tetraene
(Compound 0109)

Starting material: Compound 0409b (0.039 g, 0.05 mmol); x=3; y=0.10. δ0.58 (3 H, s), 0.85 (3 H, d, J 6.8), 1.2 to 2.1 (18 H, m), 1.35 (6 H, s), 4.36 (1 H, t, J 4.5), 5.74 (1 H, dd, J 5.5 16), 5.87 (1 H, d, J 16).

EXAMPLE 10

22(S)-Ethoxy-1(S),3(R),25-trihydroxy-20(R)-9,10-seco-cholesta-5(Z),7(E),10(19),23(E)-tetraene
(Compound 0110)

Starting material: Compound 0410b (0.040 g, 0.058 mmol); x=3; y=0.07. δ0.54 (3 H, s), 0.86 (3 H, d, J 7), 1.1 to 2.1 (17 H, m), 1.17 (3 H, t, J 7), 1.34 (6 H, s), 3.25 (1 H, m), 3.48 (1 H, m), 3.76 (1 H, dd, J 3 7), 5.58 (1 H, dd, J 7 16), 5.74 (1 H, d, J 16).

EXAMPLE 11

1(S),3(R),-Dihydroxy-20(R)-(1'(R),-5'-dihydroxy-5'-ethyl-3'(E)-hepten-1'-yl)-9,10-seco-pregna-5(Z),7(E),-10(19)-triene (Compound 0111)

Starting material: Compound 0411b (0.015 g, 0.018 mmol); x=2; y=0.05.

EXAMPLE 12

1(S),3(R),-Dihydroxy-20(R)-(1'(R)-methoxy-5'-hydroxy-5'-ethyl-3'(E)-hepten-1'-yl)-9,10-seco-pregna-5(Z),7(E), 10(19)-triene (Compound 0112)

Starting material: Compound 0412b (0.015 g, 0.021 mmol); x=2; y=0.05.

EXAMPLE 13

1(S),3(R)-Dihydroxy-20(S)-(7'-hydroxy-7'-methyl-5'(E)-octen-1'-yl)-9,10-seco-pregna-5(Z),7(E),10(19)-triene (Compound 0113)

Starting material: Compound 0413b (0.034 g, 0.05 mmol); x=3; y=0.21. δ0.54 (3 H, s), 0.83 (3 H, d), 1.05 to 2.1 (25 H, m), 1.3 (6 H, s), 5.6 (2 H, m).

EXAMPLE 14

1(S),3(R),-Dihydroxy-20(S)-(4'-hydroxy-4'-cyclopropyl-2'(E)-buten-1'-yl)-9,10-seco-pregna-5(Z),7(E),10(19)-triene (Compound 0114)

Starting material: Compound 0414b (0.035 g, 0.053 mmol); x=3; y=0.15. δ0.22 (1H, m), 0.32 (1H, m), 0.5 (2H, m), 0.56 (3H, s), 0.83 (3H, d), 0.98 (1H, m), 2.34 (1H, m), 3.46 (1H, m), 5.52 (1H, dd), 5.62 (1H, dt).

EXAMPLE 15

1(S),3(R),-Dihydroxy-20(S)-(5'-hydroxy-5'-ethyl-2'(E)-hepten-1'-yl)-9,10-seco-pregna-5(Z),7(E),10(19)-triene (Compound 0115)

Starting material: Compound 0415b (0.050 g, 0.073 mmol); x=3; y=0.18.

EXAMPLE 16

1(S),3(R),-Dihydroxy-20(S)-(6'-hydroxy-6'-ethylocta-2'(E),4'(E)-dien-1'-yl)-9,10-seco-pregna-5(Z),7(E),-10(19)-triene (Compound 0116)

Starting material: Compound 0416b (0.052 g, 0.075 mmol); x=3; y=0.20.

EXAMPLE 17

Capsules Containing Compound 0110

Compound 0110 was dissolved in arachis oil to a final concentration of 1 μg of Compound 0110/ml oil. 10 Parts by weight of gelatine, 5 parts by weight glycerine, 0.08 parts by weight potassium sorbate, and 14 parts by weight distilled water were mixed together with heating and formed into soft gelatine capsules. These were then filled each with 100 µl of Compound 0110 in oil solution, such that each capsule contained 0.1 µg of Compound 0110.

EXAMPLE 18

Dermatological Cream Containing Compound 0110

In 1 g almond oil was dissolved 0.05 mg of Compound 0110. To this solution was added 40 g of mineral oil and 20 g of self-emulsifying beeswax. The mixture was heated to liquify. After the addition of 40 ml hot water, the mixture was mixed well. The resulting cream contains approximately 0.5 µg of Compound 0110 per gram of cream.

What we claim is:

1. A compound of formula I

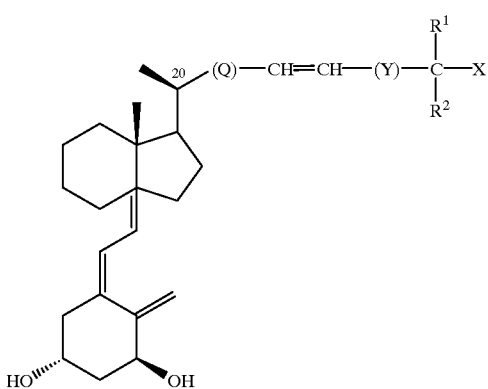

in which formula X is hydrogen or hydroxy; $R^1$ and $R^2$ stand for methyl or ethyl: Q is methylene, ethylene, tri- or tetra-methylene and may optionally be substituted with an oxy group, $-OR^3$, in which $R^3$ is hydrogen, methyl or ethyl; Y is either a single bond or $C_1$–$C_2$ hydrocarbylene where hydrocarbylene is the diradical obtained after removal of 2 hydrogen atoms from a straight, branched or cyclic, saturated or unsaturated hydrocarbon and $R^1$, $R^2$ or Y is unsubstituted or substituted by one or more fluorine atoms or a hydroxyl group.

2. A compound of formula I according to claim 1 in which X is hydroxy and Y is a single bond.

3. A compound of formula I according to claim 2 in which $R^1$ and $R^2$ are the same.

4. A diastereoisomer of a compound according to claim 1, in pure form; or a mixture of such diastereoisomers, the compound being recovered either in crystalline form directly or as a solvate or in amorphous form.

5. A compound according to claim 1 which is:

a) 1(S),3(R),25-Trihydroxy-20(S)-9,10-seco-cholesta-5(Z),7(E),10(19),-23(E)-tetraene b) 1(S),3(R)-Dihydroxy-20(S)-(6'-hydroxy-6'-methyl-4'(E)-hepten-1'-yl)-9,10-seco-pregna-5(Z),7(E),10(19)-triene c) 1(S),3(R),22(S),25-Tetrahydroxy-20(R)-9,10-seco-cholesta-5(Z),7(E),-10(19),23(E)-tetraene d) 22(S)-Ethoxy-1(S),3(R),25-trihydroxy-20(R)-9,10-seco-cholesta-5(Z),-7(E),10(19),23(E)-tetraene, e) 1(S),3(R),-Dihydroxy-20(R)-(1'(R)-methoxy-5'-hydroxy-5'ethyl-3'(E)-hepten-1'-yl)-9,10-seco-pregna-5(Z),7(E),10(19)-triene f) 1(S),3(R),-Dihydroxy-20(S)-(4'-hydroxy-4'-cyclopropyl-2'(E)-buten-1'-yl)-9,10-seco-pregna-5(Z),7(E),10(19)-triene.

6. A method for producing a compound of formula I of claim 1 in which an aldehyde which is 1(S),3(R)-bis-(tert-butyldimethylsilyloxy)-20(S)-formylmethyl-9,10-seco-pregna-5(E),7(E),10(19)-triene or 1(S),3(R)-bis-(tert-butyldimethylsilyloxy)-20(S)-(2-formylethyl)-9,10-seco-pregna-5(E),7(E),10(19)-triene or 1(S),3(R)-bis-(tert-butyldimethylsilyloxy)-20(R)-(3-formylpropyl)-9,10-seco-pregna-5(E),7(E),10(19)-triene or the corresponding derivative of one of these in which the methylene bonded to C-20 carries a methoxy, ethoxy or tert-butyl-dimethylsilyloxy substituent, is reacted either with a Wittig reagent containing a carbonyl group and the resulting product is reacted with an organo-lithium or Grignard reagent or a reducing agent, or with the lithio-derivative of an optionally hydroxylated alkyl phenyl sulphone followed by reductive elimination, to give a product, which is subjected to the arbitrary sequence of isomerization with UV-light in the presence of a triplet sensitizer (e.g. anthracene) and removal of the silyl groups with e.g. tetrabutylammonium fluoride.

7. A pharmaceutical composition containing an effective amount of one or more of the compounds of claim 1, together with a pharmaceutically acceptable, non-toxic carrier.

8. A pharmaceutical composition according to claim 7 in dosage unit form containing from 0.1 ppm to 0.1% by weight of the dosage unit of a compound of formula I.

9. In a method for inhibiting undesirable cell proliferation or for obtaining desired immunomodulating or anti-inflammatory effects in a host in need of such treatment, the improvement which comprises administering to said host an effective amount of a compound according to claim 1.

* * * * *